United States Patent [19]

Stewart

[11] Patent Number: 6,090,369

[45] Date of Patent: Jul. 18, 2000

[54] SUNSCREEN FORMULATION WITH AVOBENZONE AND METHOD FOR STABILIZING SUNSCREEN FORMULATION WHICH CONTAINS AVOBENZONE

[76] Inventor: Ernest Glading Stewart, 101 W. Club Dr., Thomasville, Ga. 31799

[21] Appl. No.: 08/868,765

[22] Filed: Jun. 4, 1997

[51] Int. Cl.[7] ...................................................... A61K 7/42
[52] U.S. Cl. .............................. 424/59; 424/401; 514/680
[58] Field of Search ...................... 424/401, 59; 514/680, 514/681, 532, 534, 844, 845, 873, 970, 972

[56] References Cited

U.S. PATENT DOCUMENTS

| | | | |
|---|---|---|---|
| 5,514,437 | 5/1996 | Tanner et al. .............................. | 424/63 |
| 5,585,090 | 12/1996 | Yoshioka et al. .......................... | 424/59 |
| 5,587,150 | 12/1996 | Deflandre et al. ......................... | 424/59 |
| 5,605,680 | 2/1997 | Deflandre et al. ......................... | 424/59 |
| 5,663,213 | 9/1997 | Jones et al. .............................. | 523/105 |
| 5,700,452 | 12/1997 | Deckner et al. .......................... | 424/59 |

*Primary Examiner*—José G. Dees
*Assistant Examiner*—Michael A. Williamson
*Attorney, Agent, or Firm*—Sanford J. Asman

[57] ABSTRACT

The invention relates to a photostable screening cosmetic composition for protecting human skin against UV rays, comprising, comprising avobenzone, octyl-methoxycinnamate, and an additional constituent, R, where R is selected from the group consisting of titanium dioxide and zinc oxide.

8 Claims, No Drawings

SUNSCREEN FORMULATION WITH AVOBENZONE AND METHOD FOR STABILIZING SUNSCREEN FORMULATION WHICH CONTAINS AVOBENZONE

BACKGROUND OF THE INVENTION

The present invention relates to sunscreen formulations. In particular, the invention relates to a sunscreen formulation containing avobenzone.

Avobenzone is a wide spectrum UVA sunscreen which has recently been approved by the Food and Drug Administration ("FDA") for use in the United States. Due to its wide spectrum it is presently the most efficient UVA sunscreen on the market. In addition to UVA protection, a sunscreen must also provide UVB protection. In that respect, octocrylene and octyl-methoxycinnamate are both known to be efficient UVB sunscreens. Accordingly, a sunscreen formulation containing avobenzone as a UVA blocker requires a UVB blocker, such as octocrylene or octyl-methoxycinnamate in order to provide protection against both UVA and UVB.

The FDA limits the amount of octocrylene in a sunscreen to no more than ten percent (10%) by weight. Similarly, the FDA limits the amount of octyl-methoxycinnamate which can be used in a sunscreen to seven and one-half percent (7.5%) by weight. Due to these limitations on the amount of either octocrylene or octyl-methoxycinnamate which the FDA permits, it is not possible to provide a sunscreen containing avobenzone and either octocrylene or octyl-methoxycinnamate which would provide a formulation having a sun protection factor ("SPF") of SPF 30. Accordingly, it is known to combine multiple UVB blocks such as octocrylene and octyl-methoxycinnamate together in a formulation which is then able to provide an overall formulation having an SPF 30.

Notwithstanding the wide spectrum UVA protection provided by avobenzone, a known problem with avobenzone is that it is photodegradable. In particular, exposure of avobenzone to light causes a degradation of its sunscreen protection capabilities. It has heretofore been found, as described in U.S. Pat. No. 5,587,150 entitled PHOTOSTABLE COSMETIC SCREENING COMPOSITION CONTAINING A UV-A SCREENING AGENT AND AN ALKYL BETA., BETA-DIPHENYLACRYLATE OR ALPHA-CYANO BETA., BETA-DIPHENYLACRYLATE which issued to A. Deflandre, et als. on Dec. 24, 1996 that by combining octocrylene with avobenzone, the avobenzone will be stabilized and degradation will be substantially eliminated. As set forth above, this combination has the further synergistic effect of adding to the UVB blocking capability of the combination while also boosting the SPF of the combination. Also, U.S. Pat. No. 5,605,680 entitled PHOTOSTABLE COSMETIC COMPOSITION CONTAINING A UV-A SCREEN AND A UV-B SCREEN AND A PROCESS FOR STABILIZING THE UV-A SCREEN WITH THE UV-B SCREEN which issued to A. Deflandre, et als. on Feb. 25, 1997 may be relevant to the present invention.

SUMMARY OF THE INVENTION

The present invention is a sunscreening cosmetic composition comprising avobenzone, octyl-methoxycinnamate, and an additional constituent, R, where R is selected from the group consisting of titanium dioxide and zinc oxide.

In a preferred embodiment of the invention, the sunscreen contains octyl-methoxycinnamate in a weight percentage of less than 7.5% by weight of the formulation.

In another preferred embodiment of the invention, the sunscreen contains octocrylene in a weight percentage of less than 10% by weight of the formulation.

In order to increase the SPF, the sunscreen of the present invention can contain octocrylene in a weight percentage of less than 10% by weight of the formulation and octyl-methoxycinnamate in a weight percentage of less than 7.5% by weight of the formulation.

DETAILED DESCRIPTION OF AN EXEMPLARY EMBODIMENT

In the course of developing a sunscreen containing avobenzone, it was discovered that by combining either zinc oxide and avobenzone or titanium dioxide with avobenzone, where both zinc oxide and titanium dioxide are known to be UVA blockers which can increase the SPF of a sunscreen formulation, it was discovered that the presence of the titanium oxide or zinc oxide had the unexpected result of stabilizing the avobenzone, without the presence of octocrylene. Accordingly, in accordance with the present invention, a novel, stable, sunscreen formulation using avobenzone, has been discovered. The formulation of the present invention combines avobenzone, octyl-methoxycinnamate, and an additional constituent selected from the group consisting of titanium dioxide and zinc oxide. In accordance with the present invention, the stabilized sunscreen of the present invention uses avobenzone, octyl-methoxycinnamate, and either titanium dioxide or zinc oxide to produce a stable formulation without need to include octocrylene.

As the FDA limits the amount of octyl-methoxycinnamate to no more than 7.5%, by weight, of the composition, and as that amount of octyl-methoxycinnamate is not sufficient to produce an SPF rating of 30, other sunscreen constituents can be included in the formulation for the sole purpose of increasing the SPF of the formulation. Accordingly, octocrylene, which can be added to the formulation in an amount up to 10% of the weight of the formulation can be added to increase the SPF to SPF 30, thereby remaining within the FDA limits with respect to not having greater than 7.5% octyl-methoxycinnamate, by weight.

It should be noted that the use of octocrylene in the present formulation is solely for the purpose of increasing the SPF and not for the purpose of stabilizing the avobenzone.

I claim:

1. A sunscreen formulation consisting of:
   (a) avobenzone;
   (b) octyl-methoxycinnamate; and
   (c) an additional constituent, R, where R is selected from the group consisting of titanium dioxide and zinc oxide, wherein the presence of the additional constituent, R, serves to prevent the degradation of the avobenzone when the composition is exposed to light.

2. The sunscreen formulation of claim 1, wherein the octyl-methoxycinnamate is present in a weight percentage not greater than 7.5% by weight.

3. The sunscreen formulation of claim 2, rather comprising octocrylene.

4. The sunscreen formulation of claim 3, wherein said octocrylene is present in an amount not greater than 10% by weight.

5. The sunscreen formulation consisting of:
   (a) avobenzone;
   (b) octyl-methoxycinnamate;
   (c) octocrylene; and
   (d) an additional constituent, R, where R is selected from the group consisting of titanium dioxide and zinc oxide, wherein the presence of the additional constituent, R, serves to prevent the degradation of the avobenzone when the composition is exposed to light.

6. The sunscreen formulation of claim 5, wherein the octyl-methoxycinnamate is present in a weight percentage not greater than 7.5% by weight.

7. The sunscreen formulation of claim 5, wherein said octocrylene is present in an amount not greater than 10% by weight.

8. A sunscreen formulation consisting of:
   (a) avobenzone;
   (b) a sunscreen which is a UVB blocker; and
   (c) an additional constituent, R, where R is selected from the group consisting of titanium dioxide and zinc oxide, wherein the presence of the additional constituent, R, serves to prevent the degradation of the avobenzone when the composition is exposed to light.

* * * * *

UNITED STATES PATENT AND TRADEMARK OFFICE
CERTIFICATE OF CORRECTION

PATENT NO : 6,090,369
DATED : July 18, 2000
INVENTOR(S): Ernest Glading Stewart

It is certified that error appears in the above-identified patent and that said Letters Patent is hereby corrected as shown below:

Claim 3, line 1, change "rather" to --further--.

Signed and Sealed this

Twenty-seventh Day of March, 2001

Attest:

NICHOLAS P. GODICI

Attesting Officer

Acting Director of the United States Patent and Trademark Office